US00PP29328P3

(12) United States Plant Patent
Noodelijk

(10) Patent No.: US PP29,328 P3
(45) Date of Patent: May 29, 2018

(54) ***CELOSIA* PLANT NAMED 'SPITENZ LIPSTICK'**

(50) Latin Name: *Celosia argentea*
Varietal Denomination: Spitenz Lipstick

(71) Applicant: Robert Noodelijk, Woubrugge (NL)

(72) Inventor: Robert Noodelijk, Woubrugge (NL)

(73) Assignee: Floritec Breeding BV (NL)

( * ) Notice: Subject to any disclaimer, the term of this patent is extended or adjusted under 35 U.S.C. 154(b) by 40 days.

(21) Appl. No.: 14/999,491

(22) Filed: May 12, 2016

(65) Prior Publication Data

US 2016/0353635 P1 Dec. 1, 2016

(30) Foreign Application Priority Data

May 26, 2015 (QZ) ..... PBR 2015/1067

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Cassandra Bright

(57) ABSTRACT

A *Celosia* plant named 'Spitenz Lipstick' characterized by its many bright red-purple colored spikes, prolific branching, foliage from the bottom to the top of the plant, a compact and symmetrical plant habit, and a response time of approximately 7.5 weeks is disclosed.

3 Drawing Sheets

Genus and species: *Celosia argentea.*
Variety denomination: 'Spitenz Lipstick'.

BACKGROUND OF THE NEW PLANT

The present invention comprises a new and distinct variety of *Celosia* plant, botanically known as *Celosia argentea*, and hereinafter referred to by the variety name 'Spitenz Lipstick'. This new variety produces many medium sized spikes with red-purple colored individual blooms and has a blooming period of about eight weeks.

The new variety 'Spitenz Lipstick' is a naturally occurring sport from the unpatented *Celosia* variety 'Innovo'. The new and distinct variety was discovered and selected as a single plant in a greenhouse in Monster, The Netherlands in May 2013.

The new variety 'Spitenz Lipstick' was first asexually reproduced by terminal vegetative cuttings in a greenhouse in Monster, The Netherlands in August 2014 and has been asexually reproduced for one and a half years. The new variety 'Spitenz Lipstick' has been found to retain its distinctive characteristics through successive asexual propagations.

SUMMARY OF THE INVENTION

The following are the most outstanding and distinguishing characteristics of the new variety when grown under normal horticultural practices in Monster, The Netherlands.

1. Red-purple spiked-type inflorescences having many spikes per branch;
2. Prolific branching;
3. Compact symmetrical plant habit
4. Foliage located all over the stem to the bottom of the plant.

COMPARISON WITH THE PARENT VARIETY

The new variety 'Spitenz Lipstick' differs from parent variety in having a brighter pink flower color. Additionally 'Spitenz Lipstick' produces more flowering spikes per plant than the parent variety.

COMPARISON WITH COMMERCIAL VARIETIES

The new variety Spitenz Lipstick differs from the commercial *Celosia* 'Spitenz' U.S. Plant Pat. No. 23,076 in flower color. Florets of the new variety are Red-Purple 61A, florets of 'Spitenz' are Purple 78A. Further, the new variety 'Spitenz Lipstick' has stems and peduncles colored near Red-Purple 58A. Stems and peduncles of 'Spitenz' are colored near Yellow-Green 147C. The new variety 'Spitenz Lipstick' has a flowering response time that is approximately one week longer than the response time of 'Spitenz'.

The new variety 'Spitenz Lipstick' can also be compared to *Celosia* 'Spitenz Dark', filed concurrently having application Ser. No. 14/999,490. 'Spitenz Lipstick' produces darker colored flowers. Further, the new variety 'Spitenz Lipstick' has on average taller spikes and more flowering spikes per plant than 'Spitenz Dark'.

DESCRIPTION OF THE PHOTOGRAPHS

This new *Celosia* plant is illustrated by the accompanying photographs which show blooms and foliage of the plant. The colors shown are as true as can be reasonably obtained by conventional photographic procedures. The photographs are of a plant that has been in bloom for approximately 3 weeks.

DESCRIPTION OF THE NEW VARIETY

Figure 1:
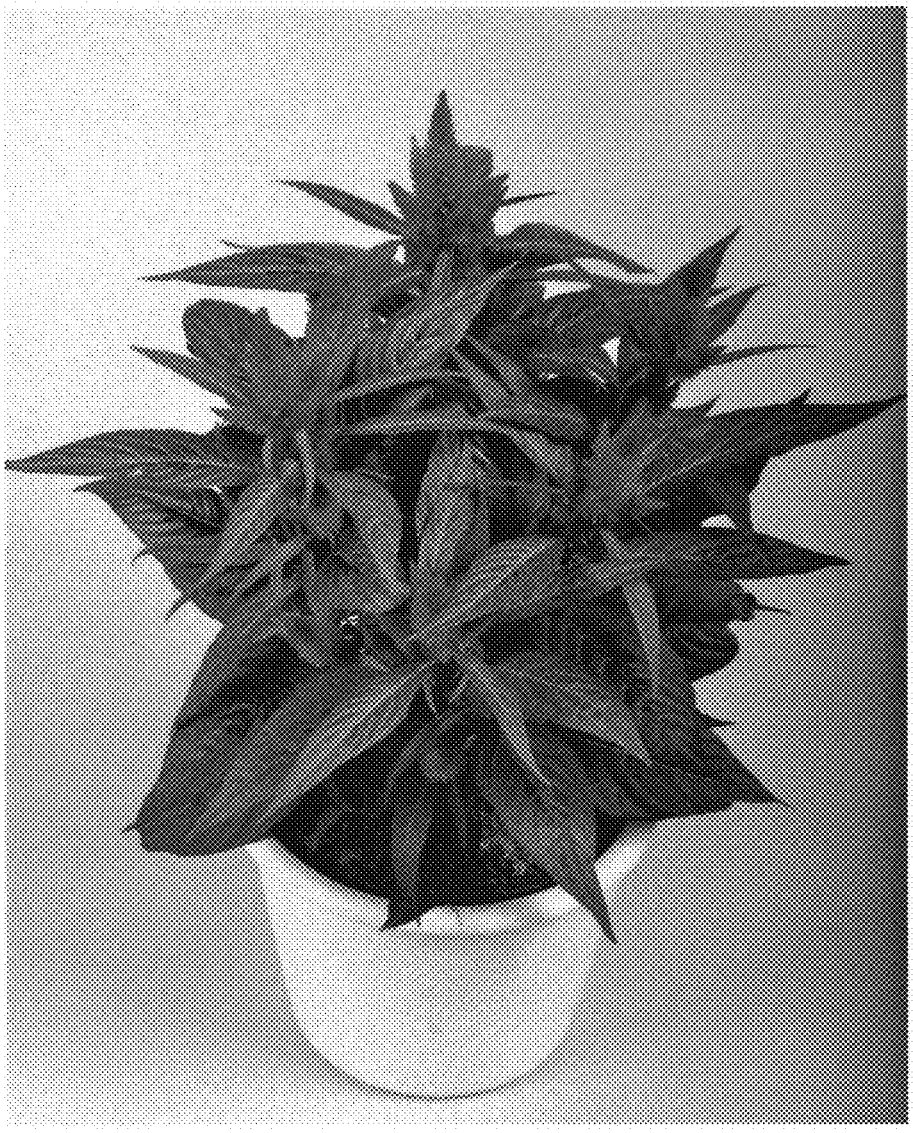
FIG. 1 shows the plant habit including the foliage and inflorescences of the new variety.
Figure 2:
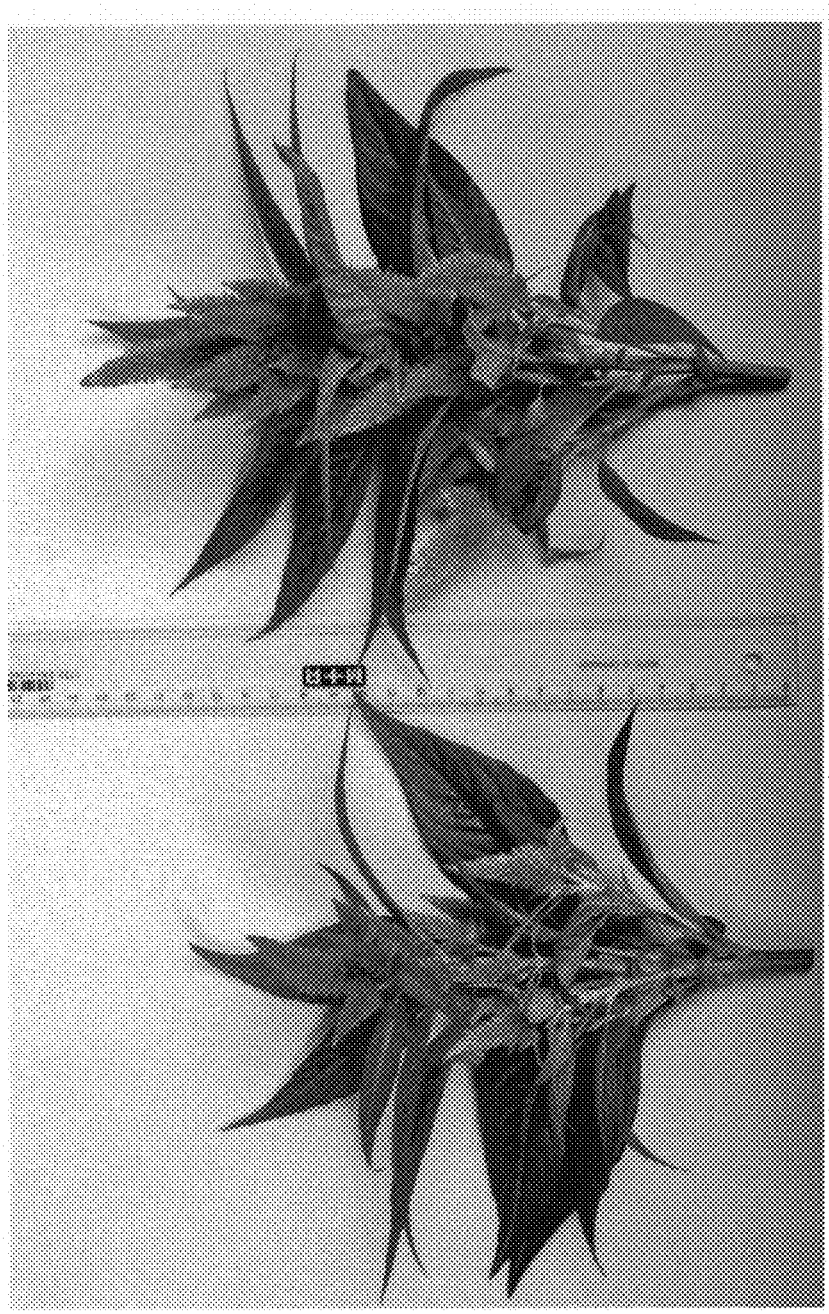
FIG. 2 is a close-up of the new variety 'Spitenz Lipstick', showing individual spikes and inflorescences per branch one week in full bloom and 3 weeks in full bloom. The larger inflorescence on the right is the 3 week old bloom.
Figure 3:
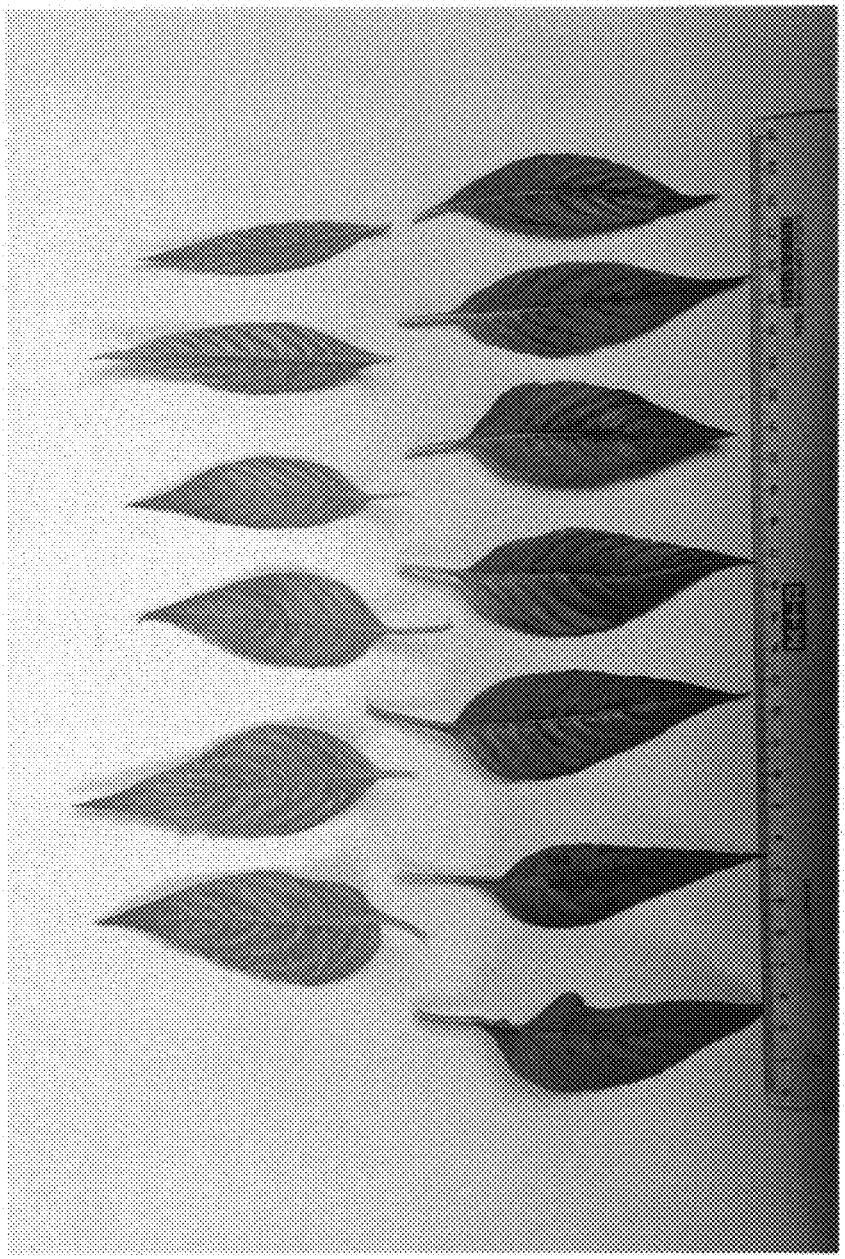
FIG. 3 is a close-up of the upper and under surfaces of the leaves of the new variety 'Spitenz Lipstick'.

The following detailed descriptions set forth the distinctive characteristics of 'Spitenz Lipstick'. The data which define these characteristics were collected from asexual reproductions carried out in Monster, The Netherlands. The plant history was taken on un-pinched plants of 8 to 10 weeks old, which were grown in 10 cm pots in a greenhouse in Monster, The Netherlands under controlled day length and temperatures. Growth retardants were used weekly. The color readings were determined under natural light. Color references are to The R.H.S. Colour Chart of The Royal Horticultural Society of London (R.H.S.), 1995 Edition.

DETAILED BOTANICAL DESCRIPTION

Classification:

*Botanical.*—*Celosia argentea.*

*Common name.*—Cockscomb, Woolflower, Feathery Amaranth.

*Denomination.*—'Spitenz Lipstick'.

Plant:

*Form.*—Rounded.

*Growth habit.*—Semi-upright, somewhat spreading symmetrical globular.

*Growth rate.*—Rapid.

*Height.*—30.0 to 32.0 cm (using weekly growth retardant).

*Width.*—20.0 to 25.0 cm (using weekly growth retardant).

Branches:

*Stem.*—Color: RHS 58A (Red-purple). Strength: Strong. Brittleness: Branches are flexible and not brittle. Cross section: Round. Texture: Smooth, no significant ribs.

*Length of lateral branch* (*from top to bottom*).—17.0 cm to 22.0 cm.

*Diameter of lateral branch.*—0.4 cm.

*Lateral branch color.*—RHS 58A (Red-purple).

*Lateral branch attachment.*—Petiolate.

*Branching.*—Average number of lateral branches: Prolific, with 4 to 8 breaks after pinching.

Leaves:

*Type.*—Single, simple.

*Arrangement.*—Alternate.

*Color.*—Upper surface: RHS 137A (Green and partially turning RHS 59A (Red) with age). Lower surface: RHS 147B (Green). Veins: RHS 45B (Red).

*Size.*—General: Medium to small.

*Immature foliage.*—Length: 7.0 cm. Width: 1.3 cm.

*Mature foliage.*—Length: 12.0 cm. Width: 3.5 cm.

*Quantity per lateral branch.*—14 to 18.

*Shape.*—Cordiform.

*Apex.*—Acuminate.

*Base.*—Attenuate.

*Margin.*—Entire.

*Texture.*—Upper surface: Leathery. Lower surface: Leathery.

Petiole:

*Color.*—Near Yellow-Green 145C flushed with anthocyanin near Red-Purple 58AC. Flushing heaviest at attachment.

*Length.*—0.4 to 0.8 cm.

*Width.*—0.2 cm.

*Venation arrangement.*—Pinnate.

Inflorescence:

*Type.*—Many small individual tubular blooms arranged together in a spike-type inflorescence.

*Height.*—1 week old spike: 3.5 to 5.0 cm. 3 week old spike: 4.0 to 7.0 cm.

*Width.*—Mature spike approximately 1.5 cm at widest point.

*Number of spikes per branch.*—14 to 20 per branch.

*Number of blooms per spike.*—1 week old spike: Approximately 70 to 100. 3 week old spike: Approximately 120 to 160.

*Performance on the plant* (*blooming period*).—8 weeks.

*Fragrance.*—Absent.

*Flower color fading.*—None.

*Peduncle.*—Length: 2.0 cm to 7.0 cm. Diameter: 0.3 cm. Color: RHS 58A (Red-purple).

*Response time.*—7.5 weeks.

Florets:

*Number of petals per floret.*—5.

*Petal texture* (*both surfaces*).—Papery.

*Apex.*—Acuminate.

*Margin.*—Entire.

*Length.*—0.5 cm.

*Width.*—0.3 cm.

*Color.*—(Both surfaces): RHS 61A (Red-Purple).

*Floral bracts.*—Not Present.

Reproductive organs:

*Stamen.*—Width: Very thin, 0.05 cm. Color: RHS 61A (Red-Purple). Pollen amount: Sparse; appears at a very late stage. Pollen color: RHS 155A (White).

*Pistil.*—Style appearance: Very thin linear. Style color: RHS 61A (Red-Purple). Style length: 0.6 cm. Stigma color: RHS 61A (Red-Purple). Stigma width: 0.1 cm.

Other characteristics

*Fruit/seed set.*—Not observed.

*Disease/pest resistance.*—Typical to known *Celosia* varieties. Neither resistance nor susceptibility to the normal diseases and pests of *Celosia* have been observed. Pests common to *Celosia* include Aphids and thrips. Typical diseases are *Botrytis* and *Pythium.*

*Temperature tolerance.*—5° C. to 38° C.

*Drought tolerance.*—No tolerance for drought.

What is claimed is:

1. A new and distinct variety of *Celosia* plant named 'Spitenz Lipstick' as described and shown herein.

* * * * *